(12) United States Patent
Grevious

(10) Patent No.: US 6,443,891 B1
(45) Date of Patent: Sep. 3, 2002

(54) TELEMETRY MODULATION PROTOCOL SYSTEM FOR MEDICAL DEVICES

(75) Inventor: John J. Grevious, Minneapolis, MN (US)

(73) Assignee: Medtronic, Inc., Minneapolis, MN (US)

(*) Notice: Subject to any disclaimer, the term of this patent is extended or adjusted under 35 U.S.C. 154(b) by 16 days.

(21) Appl. No.: 09/665,874

(22) Filed: Sep. 20, 2000

(51) Int. Cl.[7] .................... A61B 5/07; A61N 1/18; A61N 1/08
(52) U.S. Cl. ................. 600/302; 128/903; 607/32; 607/60
(58) Field of Search ................. 600/302, 300, 600/301; 128/897, 898, 903; 607/32, 60

(56) References Cited

U.S. PATENT DOCUMENTS

| | | | |
|---|---|---|---|
| 4,177,800 A | * 12/1979 | Enger | 600/302 |
| 4,681,111 A | 7/1987 | Silvian | |
| 5,127,404 A | * 7/1992 | Wyborny et al. | 607/32 |
| 5,329,260 A | 7/1994 | Poplin | |
| 5,350,411 A | * 9/1994 | Ryan et al. | 607/32 |
| 5,752,977 A | * 5/1998 | Grevious et al. | 607/32 |
| 5,767,791 A | * 6/1998 | Stoop et al. | 340/870.11 |
| 5,929,782 A | 7/1999 | Stark et al. | |
| 6,115,636 A | * 9/2000 | Ryan | 607/60 |
| 6,216,038 B1 | * 4/2001 | Hartlaub et al. | 607/31 |
| 6,263,247 B1 | * 7/2001 | Mueller et al. | 607/60 |

FOREIGN PATENT DOCUMENTS

WO     WO 96/38925     12/1996

OTHER PUBLICATIONS

International Search Report (7 pages).

* cited by examiner

Primary Examiner—Kevin Shaver
Assistant Examiner—Navin Natnithithadha
(74) Attorney, Agent, or Firm—Banner & Witcoff, Ltd.

(57) ABSTRACT

An apparatus and method for a telemetry system that automatically selects a symmetric modulation protocol configuration for telemetry communication between medical devices and programmers used in providing patient treatment. The standardized telemetry protocol will use the symmetric modulation protocol configuration to establish a downlink or uplink connection. The standardized telemetry protocol will automatically select the appropriate modulation protocol configuration depending on the modulation format and data rate capability best suited for the components needing to communicate via telemetry.

40 Claims, 9 Drawing Sheets

TELEMETRY MODULATION PROTOCOL SYSTEM FOR MEDICAL DEVICES

FIELD OF INVENTION

The present invention generally relates to implantable medical devices. More particularly, the invention relates to telemetry modulation protocols for transmitting data to and from an implantable medical device.

BACKGROUND OF THE INVENTION

The medical device industry produces a wide variety of electronic and mechanical devices for treating patient medical conditions. Depending upon the medical condition, medical devices can be surgically implanted or connected externally to the patient receiving treatment. Physicians use medical devices alone or in combination with drug therapies and surgery to treat patient medical conditions. For some medical conditions, medical devices provide the best, and sometimes the only, therapy to restore an individual to a more healthful condition and a fuller life.

Medical devices are commonly used today to treat patients suffering from various ailments. Implantable medical devices can be used to treat any number of conditions such as pain, incontinence, movement disorders such as epilepsy and Parkinson's disease, and sleep apnea. Additionally, use of medical devices appears promising to treat a variety of physiological, psychological, and emotional conditions.

One type of medical device is an Implantable Neuro Stimulator (INS). The INS is implanted at a predetermined location in the patient's body. The INS generates and delivers electrical stimulation signals at neurostimulation sites or areas to influence desired neural tissue, tissue areas, nervous system and organs to treat the ailment of concern. The stimulation sites can also include the spinal cord, brain, body muscles, peripheral nerves or any other site selected by a physician. For example, in the case of pain, electrical impulses may be directed to cover the specific sites where the patient is feeling pain. Neurostimulation can give patients effective pain relief and can reduce or eliminate the need for repeat surgeries and the need for pain medications.

An INS system generally includes an implantable neuro stimulator (INS) (also known as an implantable pulse generator (IPG)), an external physician or physician programmer, a patient programmer and at least on electrical lead. The INS can be powered by an internal source such as a rechargeable or non-rechargeable battery or by an external source such as a radio frequency transmitter. The INS contains electronics to generate and send precise, electrical pulses to the stimulation area to provide the desired treatment therapy.

The physician programmer and patient programmer are external devices that allow a physician or patient to communicate with the INS. The physician programmer is an external device that allows the physician to create and store stimulation therapy programs for the patient to be delivered by the INS. The patient programmer is an external hand-held device that allows the patient to optimize the stimulation therapy programs delivered by the INS. Typically, physician and patient programmers communicate bi-directionally with the INS, via RF telemetry signals. The bi-directional communication between the medical device and the physician or patient programmer is typically accomplished via a telemetry module. The physician programmer, the patient programmer and the medical device each have respective telemetry modules that allow for bi-directional communication between the medical device and the programmers. The bi-directional telemetry communication, between the medical device and the physician or patient programmers is typically conduced at frequencies in a range from about 150 KHz to 200 KHz using existing telemetry protocols.

Existing medical devices and programmers communicate through various telemetry protocols that are designed for the particular programmers and medical devices being used. For example, a protocol between a physician programmer and a drug pump to deliver medicine to relieve pain is usually different than a protocol for a patient programmer and an INS to deliver electrical stimulation therapy. A non-exhaustive listing of existing communication protocols include Telemetry A, Telemetry B, Brady Telemetry, etc. At present, there is no standard or uniform communications protocol for medical devices and programmers. In addition, existing protocols tend to be complex and difficult to implement in the field. As a result, existing protocols suffer reliability problems. Also, existing protocols cannot typically be interchanged for use by different products since the various existing protocols are typically product specific.

The lack of protocol standardization leads to higher costs for consumers needing such medical devices since products and protocols must be tailored to their specific needs and application. Additionally, the manufacture of products and components using the various protocols is costlier since the products cannot be efficiently produced for use with a standard protocol.

For the foregoing reasons, there is a need for a standardized telemetry communications protocol or system protocol that is simple in design, reliability and implementation. There is a need for a standardized telemetry protocol that can be used in a wide array of medical devices and programmers for patient treatment.

It is an object of the present invention to provide an apparatus and method to provide a telemetry protocol system to support and control the use of telemetry in a wide array of medical devices and products used in providing patient treatment.

It is an object of the present invention to provide an apparatus and method to provide a telemetry protocol system for use in medical devices to provide electrical stimulation therapy.

It is yet another object of the present invention to provide a standardized telemetry system that is a sophisticated and reliable design that is easy to implement at the device level and will support a wide range of medical devices.

SUMMARY OF THE INVENTION

The present invention provides an apparatus and method for a standardized telemetry system that automatically selects a modulation protocol configuration to establish a reliable symmetric telemetry link between medical devices and programmers. The modulation protocol configuration selected permits the establishment of an appropriate telemetry link and data transmission rate.

In a preferred embodiment of the present invention, the standardized telemetry protocol will automatically select a symmetric modulation protocol configuration based upon the type of hardware used to communicate between the implanted medical device and the programmer. The symmetric modulation protocol configurations are comprised of a modulation format and a corresponding data rate capability or transmission speed. Any one of the following modulation formats may be automatically selected: (1) a pulse or burst width modulation (PWM) format; a pulse or burst width modulation (PWM) plus pulse interval modulation format; (3) a modified phase shift keying (MPSK) modulation format; (4) pulse position modulation (PPM); or (5) pulse interval modulation (PIM). The corresponding data rate capability will depend on the type of communications hardware used in the devices communicating, Accordingly, a modulation protocol configuration is automatically selected that is best suited for the hardware being used to communicate between the implanted medical device and the programmer. Moreover, the modulation format used to communicate during a communications session can be continuously and contemporaneously switched from one modulation format to another.

In accordance with the present invention, there is also provided a method for establishing a communications link for transmission of information between a medical device and a programmer. The method comprises the steps of receiving a message envelope at a telemetry module, interpreting the message envelope to automatically select a symmetrical modulation protocol configuration based upon the message envelope, and establishing the communications link between to two telemetry modules using the selected modulation protocol configuration.

An apparatus and method for a telemetry system that automatically selects a symmetric modulation protocol configuration can be used with any number of programmer and medical devices requiring the use of telemetry communication, including an INS, an ENS, a pacemakers, a defibrillators, a cochlear implants, implantable diagnostic devices for detecting bodily conditions of certain organs, like the brain or the heart, and drug delivery systems having an implantable pump.

DESCRIPTION OF THE PREFERRED EMBODIMENTS

The present invention provides an apparatus and method for a telemetry system that will automatically select a symmetric modulation protocol configuration to establish telemetry communication between medical devices and their associated programmers. The standardized telemetry system is a reliable design that is easy to implement and provides a symmetric modulation protocol configuration that is best suited for the hardware used to communicate between the medical device and the programmers.

Figure 1:
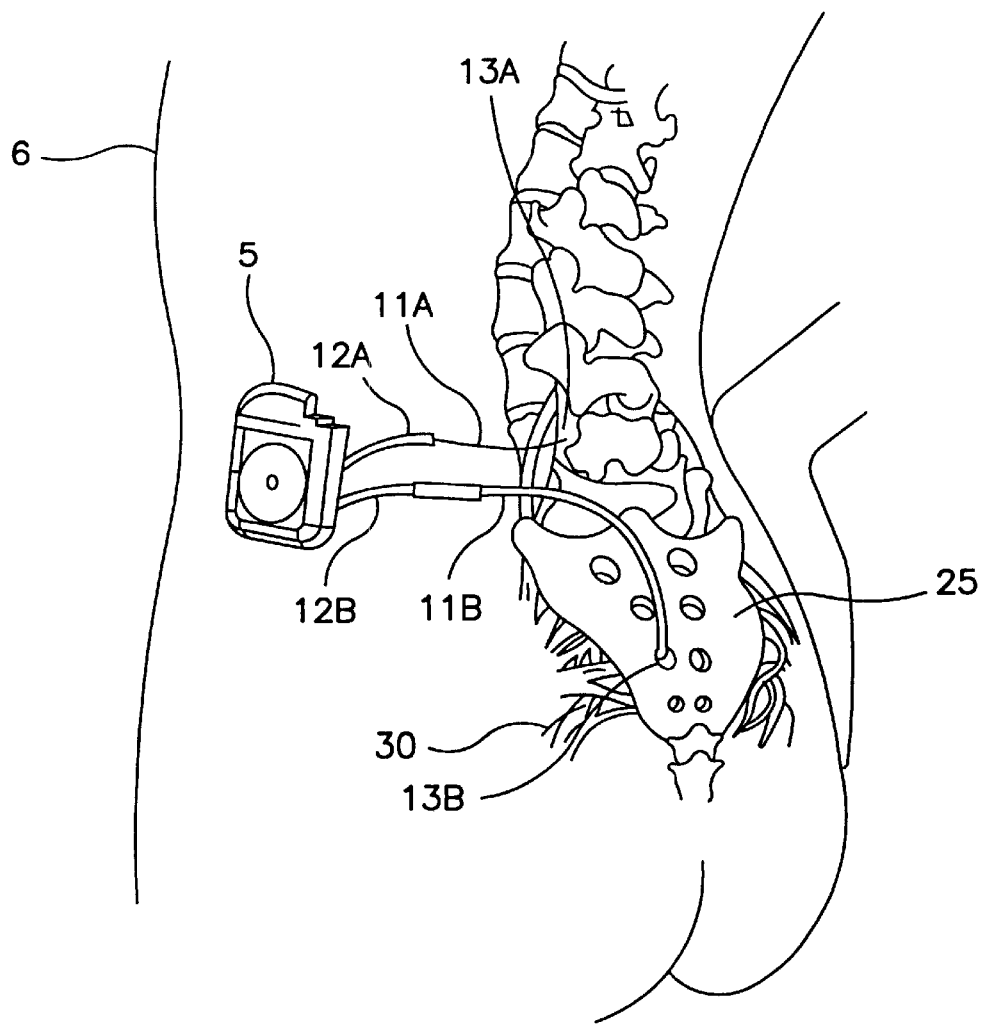
FIG. 1 illustrates a medical device as could be implanted in a human body to deliver stimulation therapy where the communications protocol of the present invention could be used.

FIG. 1 shows a general environment where a medical device such as an Implantable Neuro Stimulator (INS) 5 could be used in a patient 6. The INS 5 is preferably a modified implantable pulse generator. The INS 5 contains a power source and electronics to send precise, electrical pulses to the spinal cord, brain, or neural tissue to provide the desired treatment therapy. The INS 5 can be powered by an internal source such as a rechargeable or non-rechargeable battery or by an external source such as a radio frequency transmitter. In a preferred embodiment of the present invention, the INS 5 provides electrical stimulation by way of electrical pulses, however other forms of stimulation may be used such as continuous electrical stimulation.

The INS 5 uses one or more leads 11A and 11B and extensions 12A and 12B for delivering therapy. The leads 11A and 11B are typically surgically implanted in the patient 6. The leads 11A and 11B can be implanted and positioned to stimulate a specific site or area. Alternatively, the leads 11A and 11B may be positioned along a peripheral nerve, adjacent neural tissue, positioned to stimulate muscle tissue or other stimulation site chosen by a clinician. The leads 11A and 11B contain one or more electrodes (small electrical contacts) 13A and 13B through which electrical stimulation is delivered from the INS 5 to the targeted neural tissue. The electrodes 13A and 13B may be arranged in a predetermined physical layout. For example, where there is more than one electrode 13A and 13B the electrodes may be arranged in a linear array, in multiple linear arrays, or in a particular geometric array such as a triangle, square, rectangle, circle, etc. In addition, the INS 5 may deliver stimulation therapy signals via the electrodes in a predetermined directional sequence based on the electrode's physical layout in the stimulation area.

Figure 2:
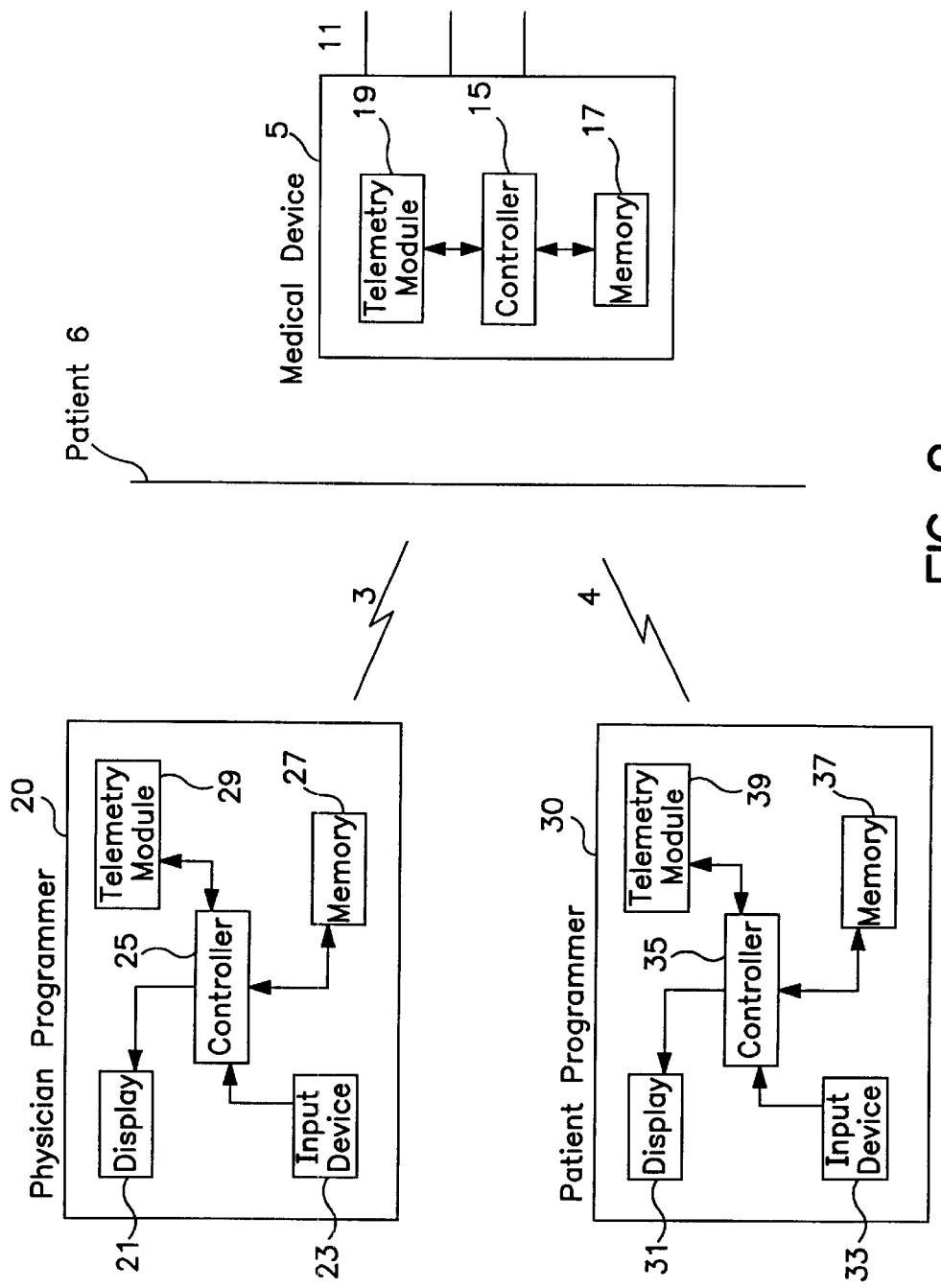
FIG. 2 shows a schematic block diagram showing a typical medical device and associated components where the communications protocol of the present invention could be used.

FIG. 2 generally depicts typical system components where the telemetry system of the present invention can be implemented to allow a medical device 5, such as the INS of FIG. 1, to communicate with associated programmers via telemetry. Depending on the hardware used, a physician programmer 20 or a patient programmer 30 can use the telemetry system of the present invention for either bi-directional or uni-directional communication with a medical device 5. Information, commands and instructions can then be communicated back and forth between the devices via telemetry 3 and 4 when in a bi-directional system. In a uni-directional system, the physician programmer 20 or patient programmer 30 communicate with the medical device 5. The medical device 5 is only a receiver, it cannot transmit information. In a preferred embodiment, the medical device 5 is implanted in the patient 6. However, those of skill in the art will readily appreciate that the telemetry system of the present invention can be used with medical devices that are internal or external to the patient.

Typically, physician and patient programmers 20 and 30 communicate with the medical device via telemetry 3 and 4 respectively. The physician and patient programmers 20 and 30 generally comprise a graphical display screen 21 and 31, an input medium 23 and 33, a physician or patient controller 25 and 35, memory 27 and 37, and a telemetry module 29 and 39. Communication with the medical device 5 is carried out through appropriate instruction entered on the physician or patient programmer input devices 23 and 33. The medical device 5 is typically comprised of memory 17 for storage of such items as therapy programs, a controller 15 for command and control of all functions of the INS 5, one or more leads 10 for delivery of treatment therapy to the body, and a telemetry module 19 for two-way communication with external devices such as physician or patient programmers 20 and 30.

Figure 3:
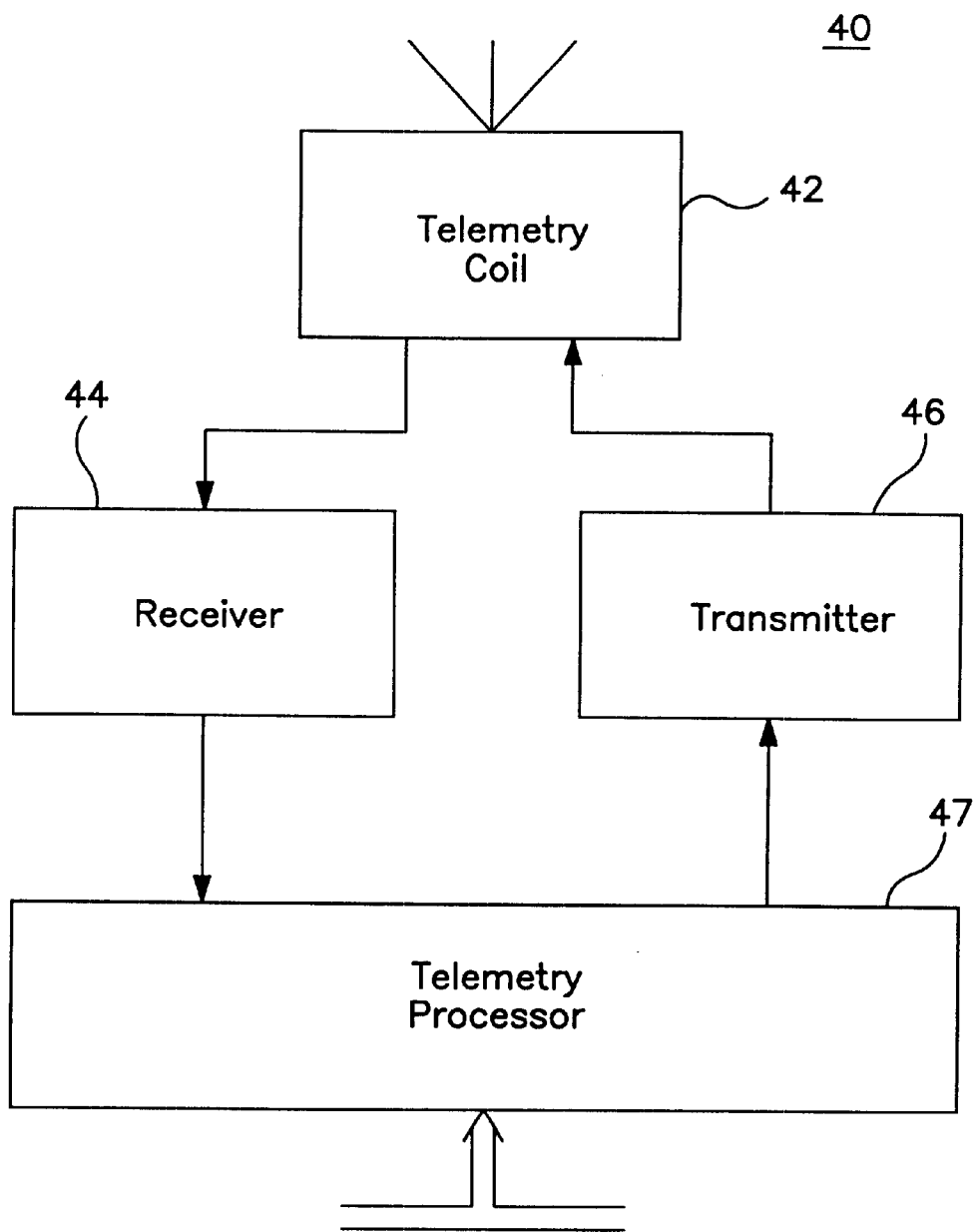
FIG. 3 shows a generic block diagram of a telemetry module such as is typically used in medical devices and programmers shown in FIG. 2.

FIG. 3 shows a block diagram of a typical telemetry module 40 that can be used in programmers 20 and 30 or medical device 5 shown in FIG. 2. The telemetry module 40 shown enables the medical device 5 and programmers 20 and 30 to communicate bi-directionally with each other via telemetry 3 and 4. The typical telemetry module 40 comprises a telemetry coil 42, a receiver 44, a transmitter 46, and a telemetry processor 47. Telemetry communication is typically conducted at frequencies in a range of about 150 KHz to 200 KHz. Those of skill in the art will readily recognize that other frequencies may be readily used.

In the typical telemetry module 40, a telemetry coil 42 that can be located inside or outside the housing of the medical device 5 or programmers 20 and 30. The telemetry coil 42 receives or transmits RF signals. When receiving, the receiver 44 provides a digital pulse representing the received RF modulated signal to the telemetry processor 47. When the telemetry communication is from a programmer 20 or 30 to a medical device 5 the process is known as downlink. When transmitting, the transmitter 46 generates a Radio Frequency (RF) modulated signal from a digital signal generated from the telemetry processor 47. When the telemetry communication is from a medical device 5 to a programmer 20 or 30 the process is known as uplink.

The telemetry processor 47 performs a variety of functions. During reception, the telemetry processor 47 can decode telemetry signals, store data into memory, and notify the device or programmer controllers 15, 25 and 35 (shown in FIG. 1) that data was received. During transmission, the telemetry processor 47 provides logic necessary to request the controllers 15, 25 and 35 to read data from memory 27 and 37, encode the data for transmission, and notify the device or programmer controllers 15, 25 and 35 that the data was transmitted. The telemetry processor 47 reduces some demands on the device or programmer controller 25 and 35. This saves energy and makes the device or programmer controllers 15, 25 and 35 available for other functions.

Figures 4A, 4B:
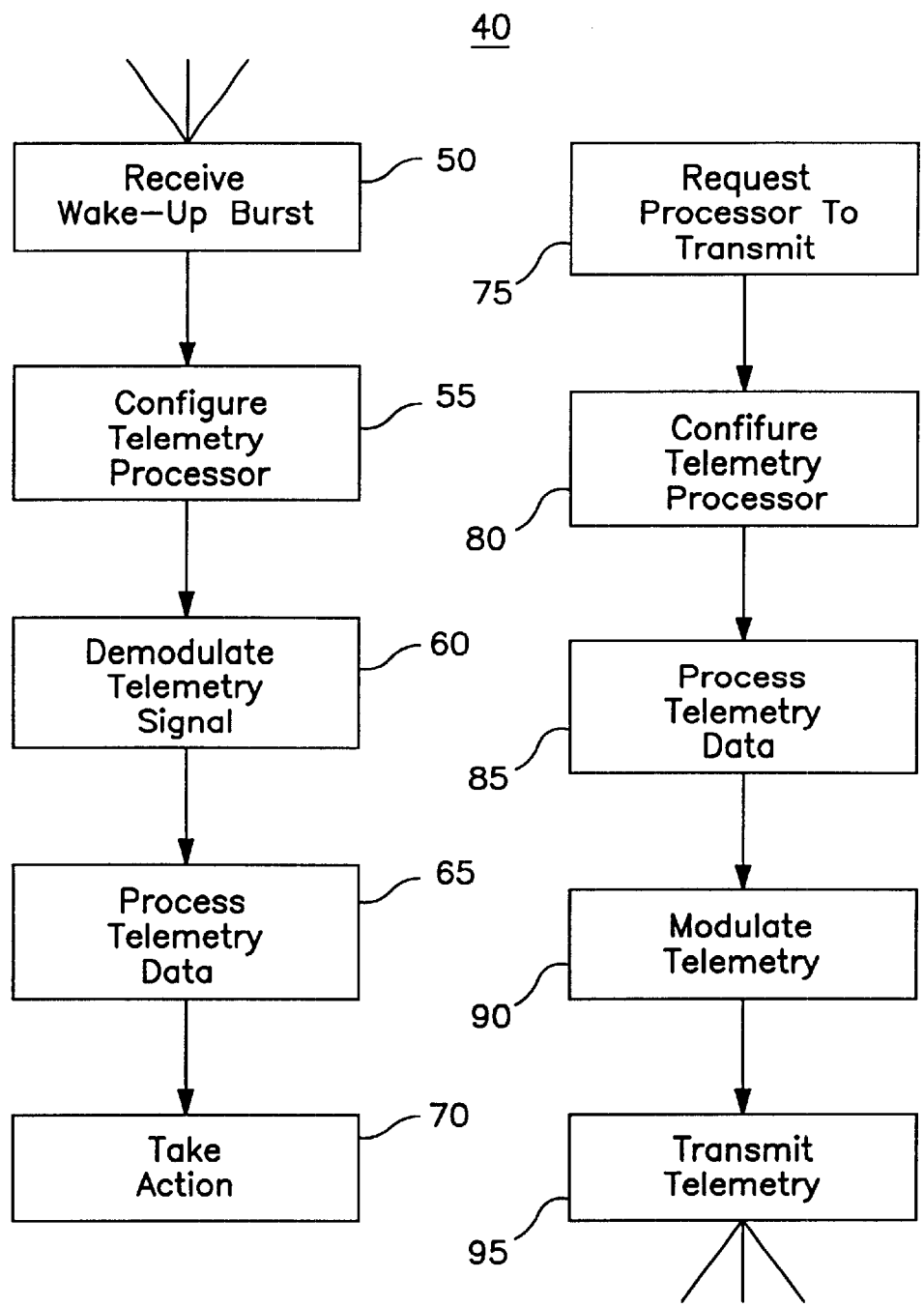
FIG. 4A shows a generic operation flowchart of the typical telemetry module shown in FIG. 3 in a receive phase.
FIG. 4B shows a generic operation flowchart of the typical telemetry module shown in FIG. 3 in a transmit phase.

FIG. 4A shows in more detail a typical telemetry operation flowchart when a medical device 5 is receiving a signal. In a first step 50, the incoming RF telemetry signal 3 or 4 is received by the telemetry coil 42 (shown in FIG. 3) and includes a wake-up burst that signals the telemetry processor 47 to prepare the telemetry processor 47 to receive incoming telemetry signals. In step two 55, the telemetry processor 47 is configured to receive a predetermined telemetry protocol that includes the type of telemetry modulation and the speed of the incoming telemetry signal. In step three 60, the telemetry receiver 44 demodulates the time base signal into digital pulses. In step four 65, the telemetry processor 47 converts/processes the digital pulses into binary data that is stored into memory. In step five 70, the medical device controller 15 will take whatever action is directed by the received telemetry signals such as adjusting stored therapy programs and therapy settings.

FIG. 4B shows in more detail a typical telemetry operation flowchart when a medical device 5 is transmitting a signal to a programmer 20 or 30 (shown in FIG. 2). In step one 75, the controller 15 (shown in FIG. 2) of the medical device 5 sends a request/command to the telemetry processor 47 to transmit data. In step two 80, the telemetry processor 47 is configured with the appropriate telemetry protocol to communicate with a programmer 20 and 30 (shown in FIG. 2). The protocol will include the type of modulation and the speed for transmission. In step three 85, the telemetry processor 47 processes the binary data into time based digital pulses. In step four 90, the transmitter 46 modulates the digital signal into an RF signal. In step five 95, the transmitter 46 transmits the telemetry signal to the programmer 20 and 30 via the telemetry coil 42 (shown in FIG. 3). It is in this environment that the telemetry system of the present invention is implemented.

A. Telemetry System Overview

The telemetry system of the present invention is a symmetrical, half-duplex communications link that uses the same inductive coupled physical transmission method to uplink and downlink. The telemetry system of the present invention is a family of related symmetrical modulation protocol configurations. The symmetrical modulation protocol configurations vary in modulation format complexity and data rate capability to match the requirements of the application and/or products being used. In a preferred embodiment, at least five modulation formats are available to create and implement the modulation protocol configurations. One of the modulation formats is pulse or burst width modulation (Format A). A second modulation format is pulse or burst width modulation (PWM) plus pulse interval modulation (PIM) (Format B). A third modulation format uses a modified phase shift keying (MPSK) modulation scheme (Format C). A fourth modulation format uses pulse position modulation (PPM). A Fifth modulation format uses pulse interval modulation (PIM). Additionally, there is a corresponding data rate transmission capability or speed for the modulation that is automatically selected for communicating between the devices.

The telemetry system is a poll-response or stop-and-wait type system. The medical device 5 is the master station when communicating to a physician or patient programmer 20 or 30. While the programmer 20 and 30 is the master station when communicating to a medical device 5. Medical device 5 uplink messages will be in response to a programmer-downlinked request. One exception is waveform data. When enabled by a downlinked command, waveform data packets will be uplinked at regular (programmed) intervals instead of uplinking upon discrete requests.

B. Operation Modes

The telemetry system operates in two modes: session mode and direct mode. Programmers can operate in either mode and can uplink or downlink data in either mode. Physician programmers will typically use session mode while patient programmers will perform most of their communications in direct mode. Session mode is intended for use where communications will be maintained for a relatively long period of time, for example, a few minutes to ½ hour. Direct mode can be used where the user wishes to set up only a single or few parameters changes before moving the programmer within range of the medical device.

In session mode, a session is initiated via a downlink signal. The medical device 5 is designed to turn on go its receiver can periodically listen for downlink signals. To initiate a session the programmer will broadcast a medical device ID request. All medical devices within range of the device ID request will uplink their medical device ID. The medical device ID can include model number, sub-model, serial number and link status information. The user may then select the appropriate medical device via the programmer.

Once a session is established, the medical device 5 is in control and downlink of programming commands may begin. Periodic message exchanges between the instrument and the device will maintain the session. Link status is included in all messages. Link status is information about the telemetry communications link, e.g., whether a link is active or established so that information or commands may be transmitted.

The session is terminated upon receipt of a Close Session request from the programmer or upon expiration of the session "time-out" period. If communication is lost and reestablished within the session time-out, the session will continue. If the session time-out timer expires any partial or incomplete programming received from the instrument will be discarded.

Figure 5:
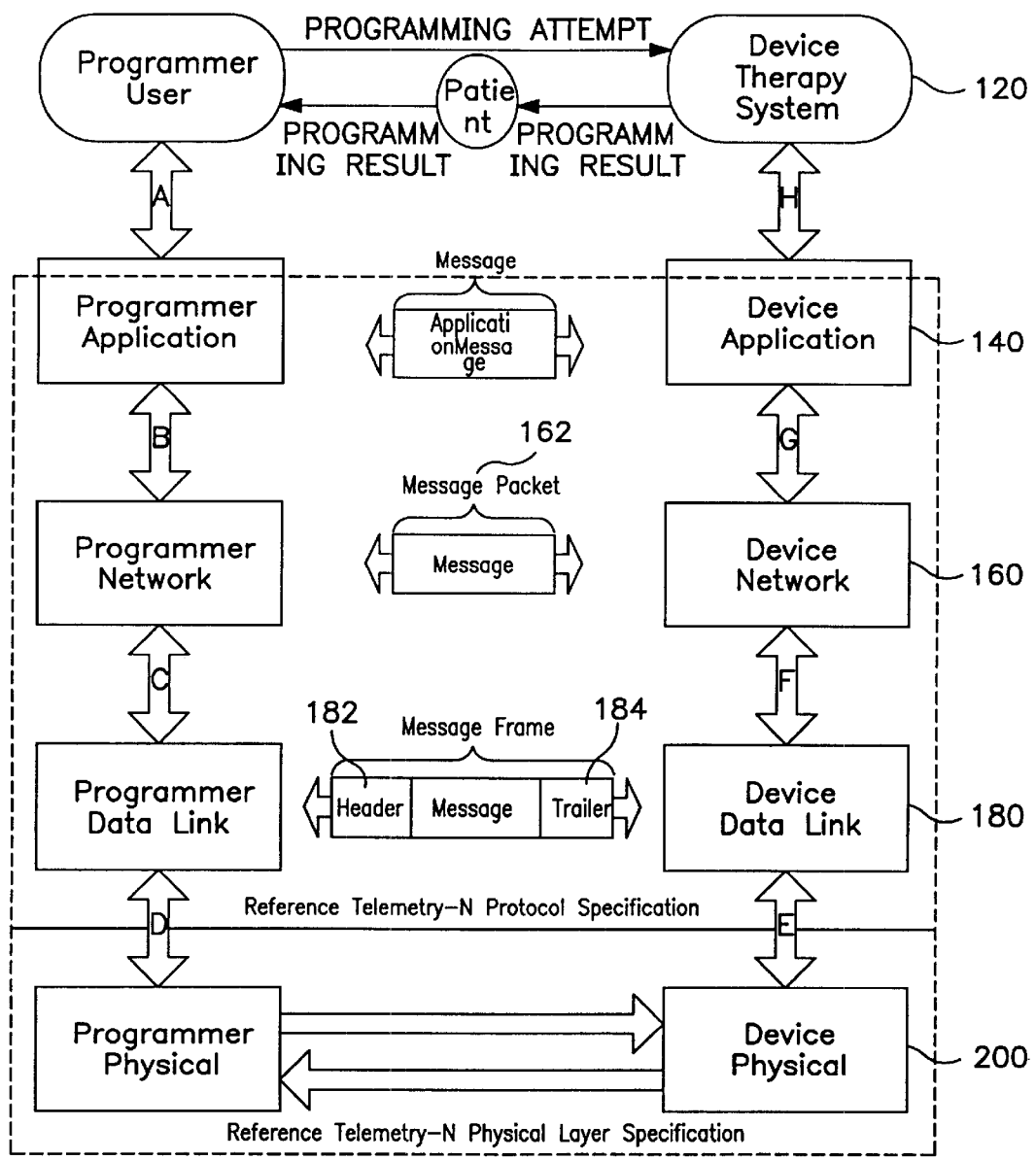
FIG. 5 shows top-level system layers of a preferred embodiment of the telemetry system of the present invention.

In direct mode, a patient programmer will be programmed with the device ID of the target medical device and will (in normal operation) communicate with only that device. When triggered by the patient, the patient programmer will begin transmitting a specific request at a periodic interval. This will continue until a response is received from the target device or the patient decides to abandon the operation C. Hierarchical Layers of the Telemetry System FIG. 5 shows a system level representation of a preferred embodiment of the telemetry system 100 of the present invention. In a preferred embodiment, the telemetry system 100 is comprised of five hierarchical system layers; a system use layer 120, an application layer 140, a network layer 160, a data link layer 180, and a physical layer 200. In the telemetry system, the various layers shown in FIG. 4 perform various well-defined functions.

1. System Use Layer

The system use layer 120 relates to user metrics, i.e., to the real world visual, auditory and perceptible results perceived by the user, be it a physician or patient. By defining the system use layer 120 in the operative communication model user and product interactions can be identified and operational dependencies can be managed. This level of system specification helps assure design coordination between various product development disciplines.

2. Application Layer

The application layer 140 is the highest protocol layer defined for the telemetry N system. The application layer 140 is the interface between the medical device applications firmware and the medical device or physician/patient programmer. The applications layer 140 can transfer and receive information from the system use layer 120 and the network layer 160 to which it is connected. Changes to the lower layers have no effect on the applications layer 140 protocol. Some specific functions performed by the applications layer 140 in the telemetry system are communications of applications messages, uplink of request confirmation (Accept/Reject), and application specific command processing.

3. Network Layer

The network layer 160 of the telemetry system has two basic two functions: to establish and manage session mode, i.e., direct or session mode, and to handle message data that exceeds the size of message "packets".

The network layer 160 can transfer and receive information from the application layer 140 and the data link layer 180 to which it is connected. The applications layer 140 will pass a message to be transmitted to the network layer 160.

The network layer 160 will attach a prefix to the message creating a message packet 162 that is then passed to the data link layer 180 for transmission. The exception to this is large block transfer operations. For these types of operations the network layer 160 is tasked with breaking the transfer up into manageable blocks and controlling the transfer of those blocks. Other functions performed by the Network Layer 160 in the telemetry system are translating between packets and messages and communication of protocol messages.

4. Data Link Layer

The data link layer 180 defines the basic transmitted message structure for the telemetry system. The physical data transmission formats (described below with reference to FIGS. 7–9) utilize bit-synchronous transmission methods that eliminate the need for message based resynchronization. This allows the Telemetry system data link or "message frame" protocol to be simpler than a more traditional synchronous protocol such as SDLC. It also does away with the start/stop bit overhead required by asynchronous transmissions.

The data link layer 180 can transfer and receive information from the network layer 160 and the physical layer 200 to which it is connected. During a transmit operation the data link layer 180 will be passed a message from the network layer 160. The data link layer 180 will simply add the data link "wrapper", i.e., a header 182 and a trailer 184, around that message and pass the result to the physical layer 200. During message reception, the data link layer 180 will accept a message from the physical layer 200, verify the information in the data link "wrapper", acknowledge receipt of the message to the sender, remove the data link wrapper from the message and pass the remaining data up to the network layer 160.

Some other functions performed by the data link layer 180 in the telemetry system are channel management, channel security, address recognition, error control, waveform transmission, and link maintenance feedback.

5. Physical Layer

The physical layer 200 defines the signal characteristics and operational limits of the telemetry communications link. Some of the essential functions performed by the physical layer 200 in the telemetry system are: physical signal transmission and reception, detection of incoming message (device wake-up), configuration switching as directed by the incoming message, and feed back on the "strength" of the link. The layers described above comprise a preferred embodiment of a telemetry system 100 of the present invention. It will be readily apparent to those skilled in the art that more or less layers could be used to define the telemetry system and that there may be other functions that are performed by the layers in the telemetry system 100.

D. System Data Flow

The flow of system data, e.g., information, instructions, or commands, in the telemetry system 100 occurs via downlink or uplink transmissions within each of the operation modes.

Downlink messages or transmissions perform a variety of functions. The functions include: programming, memory transfer, block transfer and link protocol. In the telemetry system, these functions are defined as follows:

1. Programming—are downlinks that control the operation of the medical device. This would include messages that alter or enable therapy. This type of message originates in the application layer 140.

2. Memory transfer—read or writes of limited amounts of RAM or FLASH resident data. That is, memory transfers that can be contained within one message. This type of message originates in the application layer 140.

3. Block transfer—read or writes of large blocks of data or executable code to RAM or FLASH. These may be single or multi-message transfers that must be assembled and verified by the receiver before deployment. This type of message originates in the application layer 140, but is handled primarily by the network layer 160.

4. Link control—are operations that control the medical device communications. Examples would be the acknowledgment of received transmissions, requests for retransmission and link status or "handshake" messages. Link control messages originate largely in the data link layer 180 and possibly even the network layer 160.

Referring again to FIG. 4, downlink messages originate in the data link 180 or application 140 layers. Downlink messages that are generated in response to a physician or patient action originate in the application layer 140. Telemetry link control commands such as handshake requests are generated programmatically, usually based on time, by the data link layer 180.

Initially, the physician or patient initiates a downlink in the system user layer 120. The communication processing elements, i.e., the telemetry module 19 (shown in FIG. 2), in the medical 5 device begin formatting the request for transmission. The application layer 140 will assemble the command code and all of the relevant parameters into a message and will pass the message to the network layer 160. If the message is a common programming message it will be passed to the data link layer 180. If the message is a large block transfer request the network layer 160 will partition the message into packets of suitable size and that will then be passed to the data link layer 180.

The data link layer 180 adds header 182 and trailer 184 information onto the packet and passes the completed message "frame" to the physical layer 200 for transmission. The frame header 182 contains destination and source address information and the trailer 184 contains a frame security check (CRC). The programmer now waits for an acknowledgement (ACK) from the medical device. If the medical device does not respond within a specified time the programmer 20 or 30 (shown in FIG. 2) will retransmit the frame. After a predetermined number of retransmissions the operation will be abandoned and a status returned to the message originator.

The medical device physical layer 200 receives the downlink frame and passes the bit stream to the data link layer 180 where the frame is assembled. The frame header 182 and trailer 184 are checked and if the frame is valid it is passed up to the network layer 160. If an invalid message is received due to an incorrect address or a frame check (CRC) error the device does not respond. When a frame is determined to be valid, an ACK (normally) is uplinked to the programmer 30 or 30. The header 182 and trailer 184 are then removed from the message and it is passed to the network layer 160. The network layer 160 determines if this packet is a complete message or part of a larger transmission. If the message is complete it is passed to the application layer 140 where it is processed. If the message is part of a larger transmission such as a memory block transfer, the network layer 140 verifies the sequence number of the packet and, if correct, places the data in the proper area of memory.

The medical device's response to a downlink may vary depending on options selected in the message type field in the downlinked message. The default response to a downlink will be an ACK generated automatically by the data link layer 180 when the message is determined to be valid. That ACK can be suppressed by setting a bit in the link control field, which is part of the header 182. This option defers the acknowledgment decision, which will be made in either the network or application layer 160 or 140. Additionally, a link control byte, also part of the header 182, allows the programmer to specify if the medical device will send an "operation complete" message at the appropriate time or if it is to wait for an additional "trigger" downlink before acting on the command.

Uplink messages are generated in response to a request from a programmer 20 or 30. The uplink may be an acknowledgement of a received message, a confirmation of a programming command, a large message in response to an interrogation request or may be a series of messages in response to a block transfer command. Generally, uplink messages are created in the application layer 140 of the medical device. When an uplink is requested, data is assembled in the application layer 140 into a response message and passed to the network layer 160. An exception to this is a medical device response to a handshake request. This response will be generated by the medical device hardware at the data link layer 180.

If the uplink contains a large amount of data due to a block transfer request, the network layer 160 will break the message into "message packets" 162. The packets are then sent to the data link layer 180 to be uplinked. The data link layer 180 creates "frames" from the packets by adding a header 182 and a trailer 184. The header 182 contains status and address information and the trailer 184 contains the frame Cyclic Redundancy Check (CRC) value.

The programmer 20 or 30 receives the bit-stream and reassembles the frames. The frame header 182 and trailer 184 are used by the data link layer 180 to verify the validity of the frame. If an invalid response frame is received a negative acknowledgement (NAK) is sent to the medical device to request re-transmission. If the frame is valid the header 182 and trailer 184 are removed from the frame. The packet is then passed to the network layer 160. The network layer 160 assembles the response and passes it to the application layer 140. The application layer 140 then passes the uplinked data to the user system layer 120 where the user can perceive the data.

E. Modulation Protocol Configuration Matrix

Figure 6:
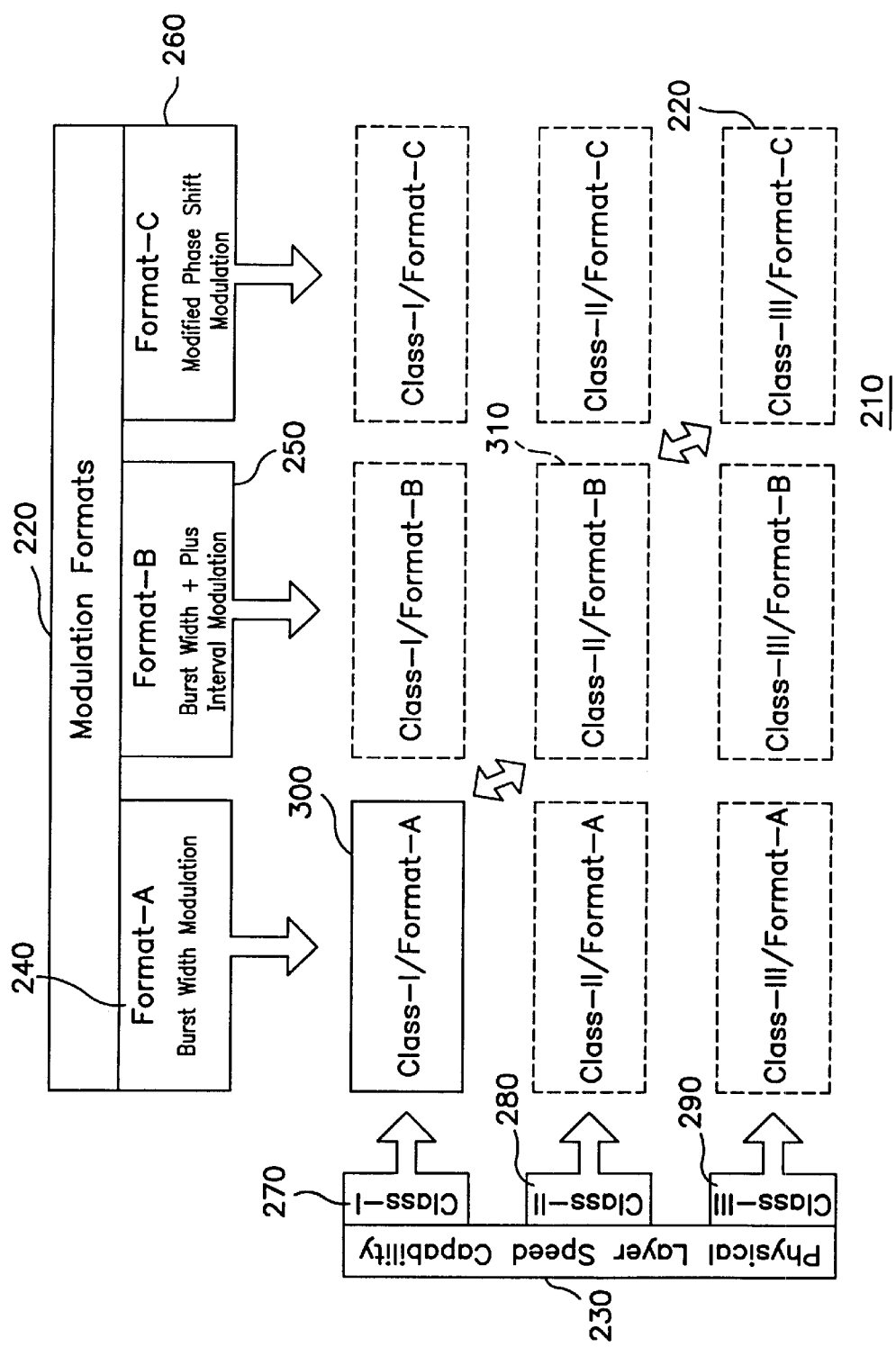
FIG. 6 shows a matrix representation of modulation protocol configurations that result from the telemetry protocol of the present invention.

FIG. 6 shows one matrix representation of possible symmetric modulation protocol configurations 210 in the telemetry system of the present invention. The modulation protocol configurations 210 relate to a particular combination of modulation format 220 and corresponding hardware speed capability class 230. In one preferred embodiment of the telemetry system, there are nine different modulation protocol configurations 210 that can provide a communications interface for a broad range of products. The modulation protocol configurations 210 are implemented as part of the physical layer 200, shown in FIG. 5.

The matrix representation shows system modulation protocol configurations for a pulse or burst width modulation format (labeled Format A), a pulse or burst width modulation (PWM) plus pulse interval modulation (PIM) format (labeled Format B), and a modified phase shift keying (MPSK) modulation format (labeled Format C). This results in a 3×3 matrix when corresponding data rate capability is included. Additional, system modulation protocol configurations are also possible for a pulse position modulation (PPM) format (not shown) and a pulse interval modulation (PIM) (not shown) and corresponding data rate capability.

The telemetry system is structured to support a variety of modulation protocol configurations 210 operating at a base carrier frequency of 175 kHz. Further, the telemetry system has automatic selection of modulation protocol configurations 210 so that the best data rate link can be established between the programmer and the medical device.

Furthermore, once a modulation protocol configuration has been automatically selected and a communications link set up with a first or initial modulation format (i.e., one of the five modulation formats mentioned), that modulation format can stay the same throughout out the entire communications session. The telemetry system of the present invention can also subsequently automatically select another modulation protocol configurations with a different modulation format, i.e., different from the initial or current modulation format, and automatically switch to the newly selected modulation format from the initial or current modulation format. The subsequent modulation format chosen is automatically selected and switched over while there is still an established communications link such that original or current communications link is not lost but merely switched "on the fly" during the current session. This switching of modulation protocol configuration can be done repeatedly to automatically select a different modulation format than the current communications link modulation format. The telemetry system automatically selects the best modulation format, and then switches "on the fly", to transmit and receive information and data in the most efficient and timely manner possible.

A modulation protocol configuration 210 is defined by a modulation format and a respective hardware data rate capability or data rate class (Class/Format). As can be seen in the chart of FIG. 6, the vertical columns define modulation formats (labeled Format A, B, and C) 220. The horizontal rows define three data rate classes 230 of varying hardware data rate capability. The data rate capabilities can be categorized as low, medium or high speed, or equivalently as Class I, II and III respectively (as shown in FIG. 6). For example, a low data rate for Class I would be in the range of 10 kbits/sec, a medium data rate for Class II would be in range of 30 kbits/sec, and a high data rate for Class III would be in the range of 100 kbits/sec. Those of skill in the art will readily recognize that other ranges and nomenclature is possible.

A unique modulation protocol configuration 210 is defined by a specific combination of modulation format 220 and a corresponding data rate capability 230. The unique combination will have its own particular raw data rate capability. Strict physical layer 200 and data layer 180 requirements exist for a given modulation protocol configuration 210. The operating modulation protocol configuration 210 is transparent to the network 160 and application layers 140 except for the net communication data rate.

The telemetry system comprises three preferred modulation formats labeled Format A, B and C. Format A 240 involves pulse or burst width modulation (PWM) and is considered is considered a low cost and reliable format. Format A 240, can theoretically be combined with Class I, II or III hardware, i.e., a low, medium or high speed data rate capability, to form modulation protocol configurations 210 in the telemetry system of the present invention. However, in a preferred embodiment, Format A 240 is preferably combined with hardware with low data rate capability in Class I 270. For example, NS1 products will utilize this configuration (e.g., '8840). Such a modulation protocol configuration 300, i.e., a Class-I/Format A combination, could be preferably labeled "Configuration-1". The Configuration-1 protocol 300 can be used in both direct and session modes and is targeted to operate at a speed of about 10 kbps.

Format B 250 uses pulse or burst width modulation (PWM) plus pulse interval modulation (PIM) and is considered a "performance" format. The Format B 250 modulation format can also theoretically be combined with Class I, II or III hardware, i.e., a low, medium or high speed data rate capability, to form modulation protocol configurations 210 in the telemetry system. In a preferred embodiment, Format B 250 is preferably combined with hardware with a medium data rate capability in Class II 280. For example, NS2 products will utilize this configuration. Such a second modulation protocol configuration 310, i.e., a Class-II/Format B combination, could be preferably labeled "Configuration-2". The Configuration-2 protocol 310 is can be used in session mode and at a speed of greater than 20 kbps.

Format C 260 involves modified phase shift keying (MPSK) modulation and is considered a "high performance" format. Format C 260, can again be theoretically combined with Class I, II or III hardware, i.e., low, medium or high speed data rate capability, to form a modulation protocol configurations 210 in the telemetry system. In a preferred embodiment, modulation Format C 260 is preferably combined with hardware with a high data rate capability in Class III 290. For example, implantable products that require large data transfer, such as possible epilepsy therapy, may utilize this configuration. Such a modulation protocol configuration 320, i.e., a Class-III/Format C combination, could be preferably labeled "Configuration-3". The Configuration-3 protocol 320 can be used in products and applications that require real time data and other functions and is targeted to operate at a speed of greater than 87 kbps. Those skilled in the art will readily appreciate that six other modulation protocol configurations are possible to address pragmatic business and product needs, though three configurations are preferred. Other modulation formats are also possible as already mentioned, e.g., for a pulse position modulation (PPM) format (not shown) and a pulse interval modulation (PIM) (not shown) which will have corresponding data rate capability.

Additionally, in a preferred embodiment, Formats A, B, and C are inherently synchronous transmission formats. This means that the data and receive clock information are transmitted together. Formats A and B allow the receive clock to be resynchronized on every bit which eliminates the need for encoding schemes such as NRZI and supporting protocols such as SDLC. Format C is defined as a "modified" phase shift keying (PSK) protocol. PSK normally does not provide receive clock resynchronization for all combinations of data. Therefore, the telemetry system of the present invention requires a modified form of this modulation method for format C to be implemented, such as burst mode transmission of PSK data.

Moreover, another feature of the telemetry system is that all configurations 210 are symmetrical as viewed at the data layer 180 and above, i.e., the same protocol is used for uplink and downlink. The symmetrical protocol facilitates system flexibility by allowing two programmers to communicate using the telemetry system of the present invention.

Figure 7:
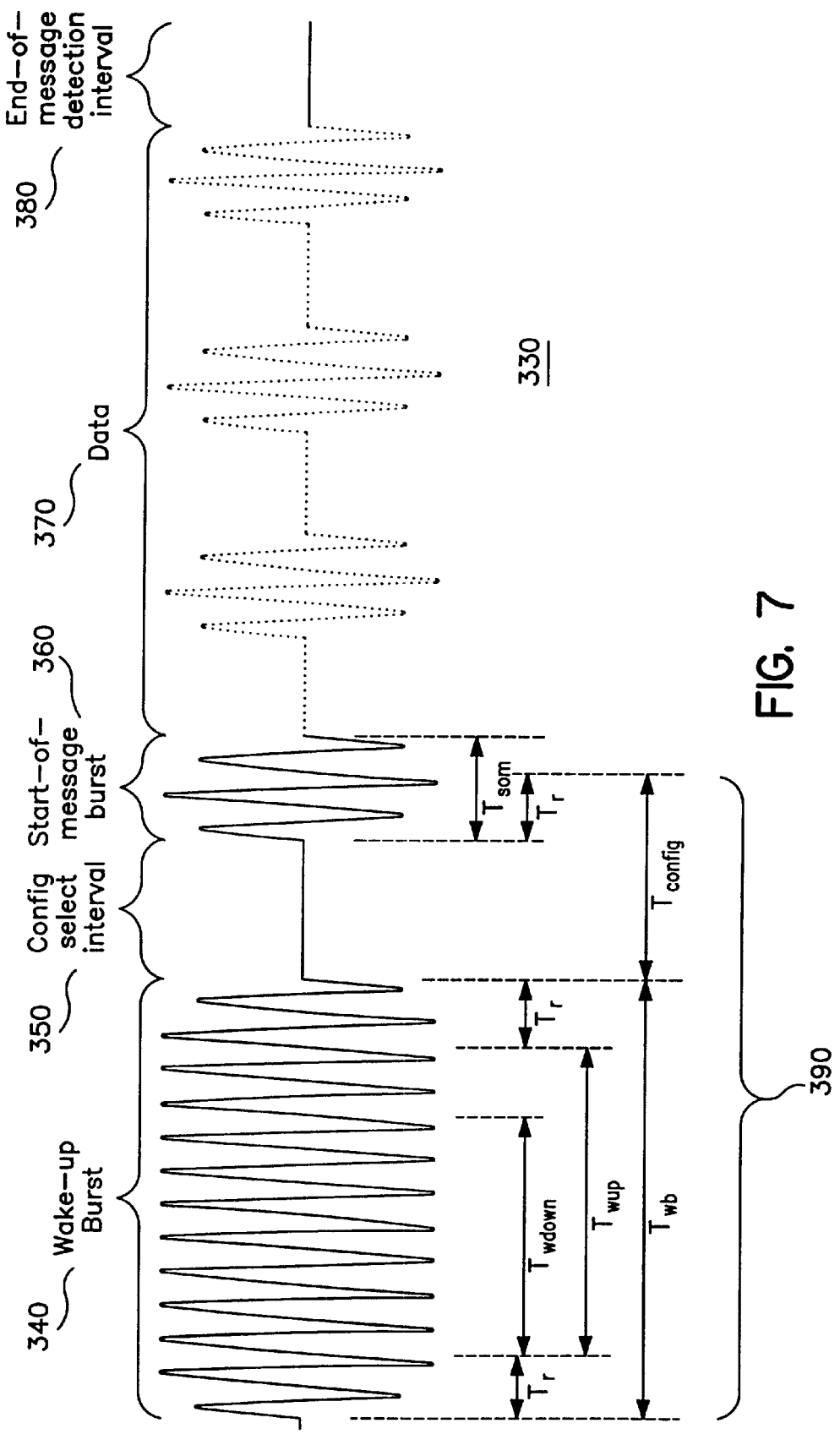
FIG. 7 shows a message envelope for Format A & B messages used in a preferred embodiment of the telemetry system of the present invention.

FIG. 7 shows a preferred message envelope 330 used for modulation Format A and B messages in the telemetry system. The message envelope is comprised of a Wake-up burst 340, a configuration select interval 350, a Start-of-Message (SOM) burst 360, data 370, and an End-of-Message (EOM) interval 380. All transmissions begin with a wake-up burst 340, a configuration select interval 350 and a Start-of-Message burst 360. These three message elements make up the message preamble 390. Messages end with an end-of-message timeout interval 380. All signal bursts are preferably 175 kHz in the telemetry system though other frequencies may be used in certain specific applications. The physical layer 200 (shown in FIG. 5) of the telemetry protocol 100 is the layer where general signaling from Wake-up Burst to End-of-Message occurs. The message preamble 390 is used to automatically determine the link-up process and the optimum modulation protocol configuration 10 (shown in FIG. 6) selection.

The front end of the message envelop 330 is the wake-up bust 340 which is the first step to initiate the link-up process to establish telemetry communication between a programmer and a medical device. All Format A and B messages, whether uplinking or downlinking, begin with a "wake-up" burst 340 as shown FIG. 7. The wake-up burst 340 will have one of two values depending on the direction (downlink or uplink) of the message. In a preferred embodiment, the wake-up burst 340 is defined as a 175 kHz signal with a interval length of $T_{wup}$ for uplinking or $T_{wdown}$ for downlinking. The receiver 44 (shown and discussed with reference to FIG. 4) will detect a wake-up burst 340 and will initialize it's receive logic to prepare for the incoming message. If the Start-of-Message (SOM) 360 bit is not received within the interval $T_{Config}$ the receiver 44 will be disabled and any further data transmissions will be ignored until the detection of another wake-up burst 340. For example and without limitation, the following table illustrates possible selection intervals for the various modes:

|  | Mode A | Mode B | Mode C |
| --- | --- | --- | --- |
| Class I | 100 uS | 250 uS | 400 uS |
| Class II | 150 uS | 300 uS | 450 uS |
| Class III | 200 uS | 350 uS | 500 uS |

Wake-up detection will differ slightly at the respective telemetry modules for physician or patient programmers and medical devices. The programmers will detect $T_{wup}$ for uplinking as a distinct interval as defined above. The medical devices, however, will identify a wake-up when receiving a burst that is greater than $T_{wdown}$ for downlinking. Detection of a valid wake-up burst followed by no data will initiate transmission of an ID message from the medical device to the programmer. The ID message response will be uplinked in a default telemetry mode. The default telemetry mode is the modulation protocol configuration labeled "Configuration-1" in FIG. 6.

Additionally, the length of the wake-up burst ($T_{wdown}$) is many times longer than the longest data bit time interval. This will allow the medical device to detect a downlink message if uplink is in progress. This is a feature of the telemetry system that provides a means to preempt a long uplink message with a higher priority downlink such as an emergency programming command.

Automatic modulation protocol configuration selection is initiated once the wake-up burst has 340 has initiated the link-up process for communication between a programmer and a medical device. Automatic modulation protocol configuration selection is done automatically by appropriate cooperation of the respective telemetry modules 39 and 19 (shown in FIG. 2) of the programmer 30 and the medical device 5. In a preferred embodiment, a Configuration select interval 350 and a Start-of-Message burst 360 together are encoded with information that determines which telemetry modulation protocol configuration 210 will be used to communicate. The encoding information indicates what modulation format and data rate speed the ensuing data 370 will have. The telemetry module 19 of the receiving medical device will decode Identification Structure (ID Structure) information contained in both the $T_{config}$ select interval 350 and the Start-of-Message burst 340 to automatically select the appropriate modulation protocol configuration 210. The intervals are preferably a function of the burst cycle time, which is 5.71 microSeconds/cycle.

If the receiving hardware in the medical device receives a message with an invalid configuration select interval it will simply not respond. In a preferred embodiment, the selection intervals for the various configurations can range from about 34–150 $\mu$S.

Generally, telemetry communication will be initiated in modulation format A with a corresponding data rate capability of Class I. In a preferred embodiment, the Format A/Class-I configuration is the default modulation protocol configuration for the telemetry system of the present invention. However, those of skill in the art will readily recognize that another configuration could be used as the default configuration. The telemetry communication can then automatically switch to another modulation protocol configuration after the medical device involved has been identified and is determined to be capable of operation in a different format and data rate capability. Since the configuration information is carried with the message, the programmer may elect to send some messages in one configuration and send others in a higher performance configuration. When a medical device receives a message it will transmit its response back to the programmer (i.e., uplink) in the same configuration, i.e., the uplink and downlink are symmetrical. When the message sequence has been completed, a new message sequence can be initiated from the programmer. The new message can have the same or different telemetry modulation protocol configuration than a prior message.

The Start-of-Message (SOM) burst 360 marks the end of the message preamble 390 prior to the transfer or flow of data. The SOM burst 360 has an interval length, $T_{som}$, which in a preferred range is about 15–150 $\mu$S. The SOM burst 360 has essentially three functions. First, the SOM burst 360 marks along with the configuration select interval 350 together are used to determine which modulation protocol configuration 210 is selected/used (as discussed above). Second, by modulating the SOM burst width, it may be used to convey data to the receiving demodulator. Last, the end of the SOM burst functions as the start of the data bit timing.

Once the SOM burst ends, the next step is the detection of data burst for the transfer or flow of data 370. Data 370 flow will be carried out via preferred modulation formats A, B or C (discussed with reference to FIGS. 7 and 8) with corresponding data rate capability hardware. Format A involves pulse or burst width modulation (PWM) and is preferably used in combination with Class I data rate capability hardware medical devices. Format B involves pulse or burst width modulation (PWM) plus pulse interval modulation (PIM) and is preferably used in combination with Class II data rate capability hardware medical devices. Last, format C involves modified phase shift keying (MPSK) modulation and is preferably used in combination with Class III data rate capability hardware medical devices. As discussed previously, other modulation formats can be used, e.g., for a pulse position modulation (PPM) format and a pulse interval modulation (PIM).

The next step for a complete message is detection of an End-of-Message (EOM) interval 380. All format A and format B messages will signal an end of message by a predetermined time interval $T_{EOM}$ (shown in FIGS. 8 and 9).

If the receiver does not detect a data burst within a specified period of time or interval (from the last data burst) End-of-Message will be assumed. The timing for EOM will vary depending on the format used.

Figure 8:
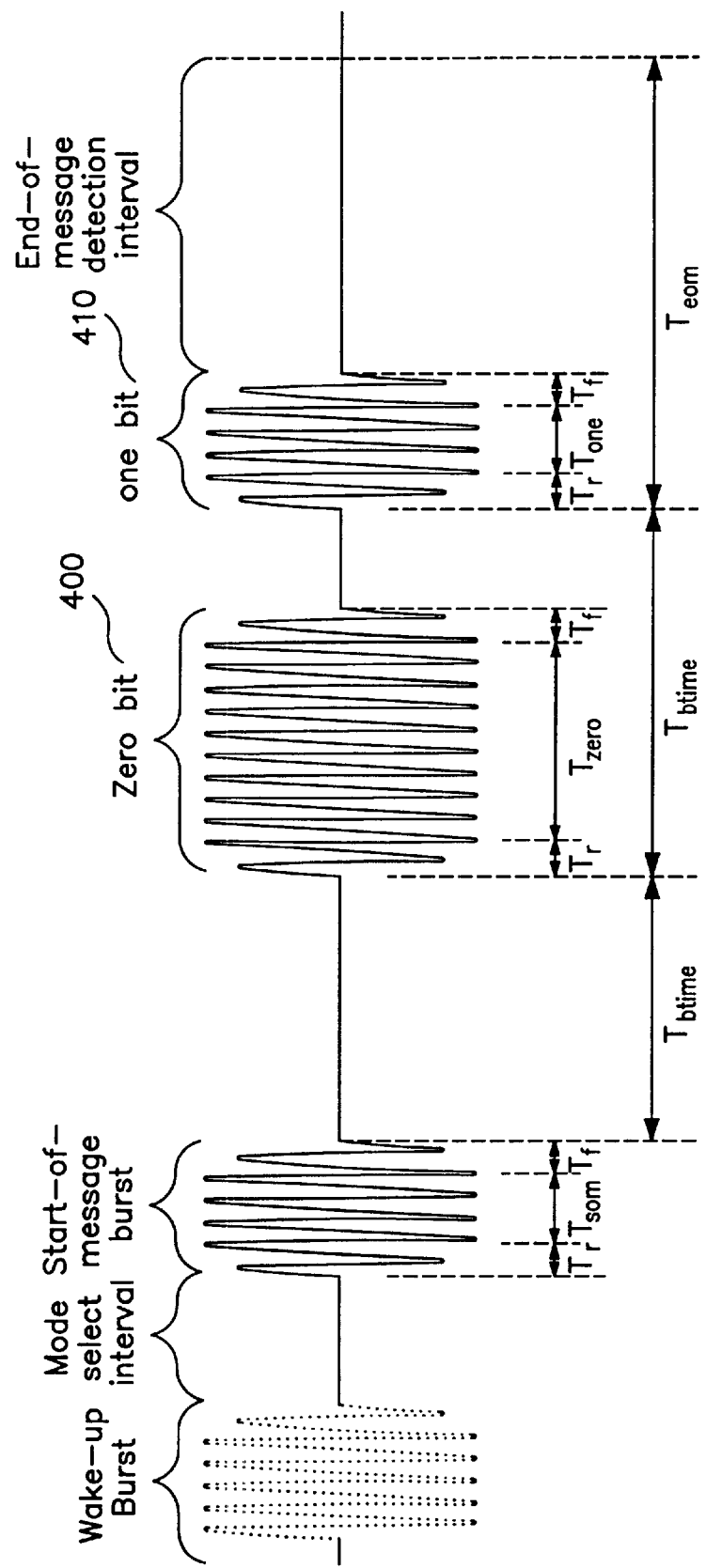
FIG. 8 shows in greater detail a preferred configuration for the data portion of the message envelope for Format A communication in the telemetry system of the present invention.

FIG. 8 shows in greater detail a preferred format for the data 370 portion of a message envelope 330 (shown in FIG. 7) for modulation Format A communication in the telemetry system of the present invention. Format A uses pulse or burst width modulation (PWM) and is preferably used in combination with medical devices having a data rate capability of Class I. The data transmissions using Format A are based on variable width bursts of 175 kHz transmitted at a constant rate. A burst width of $T_{zero}$ for a Zero bit 400 represents a "0" value. While, a burst width of $T_{one}$ for a one bit 410 represents a "1" value. The bursts are transmitted at a regular rate $T_{btime}$ that produces a raw bit rate of about 10,000 bits per second. Format A is the simplest and most reliable of the system modulation formats. In a preferred embodiment, the Format A/Class I combination is the default communication modulation protocol configuration for the telemetry system. All telemetry system compatible programmers and medical devices will support this configuration, which is labeled "Configuration-1" in FIG. 6.

Figure 9:
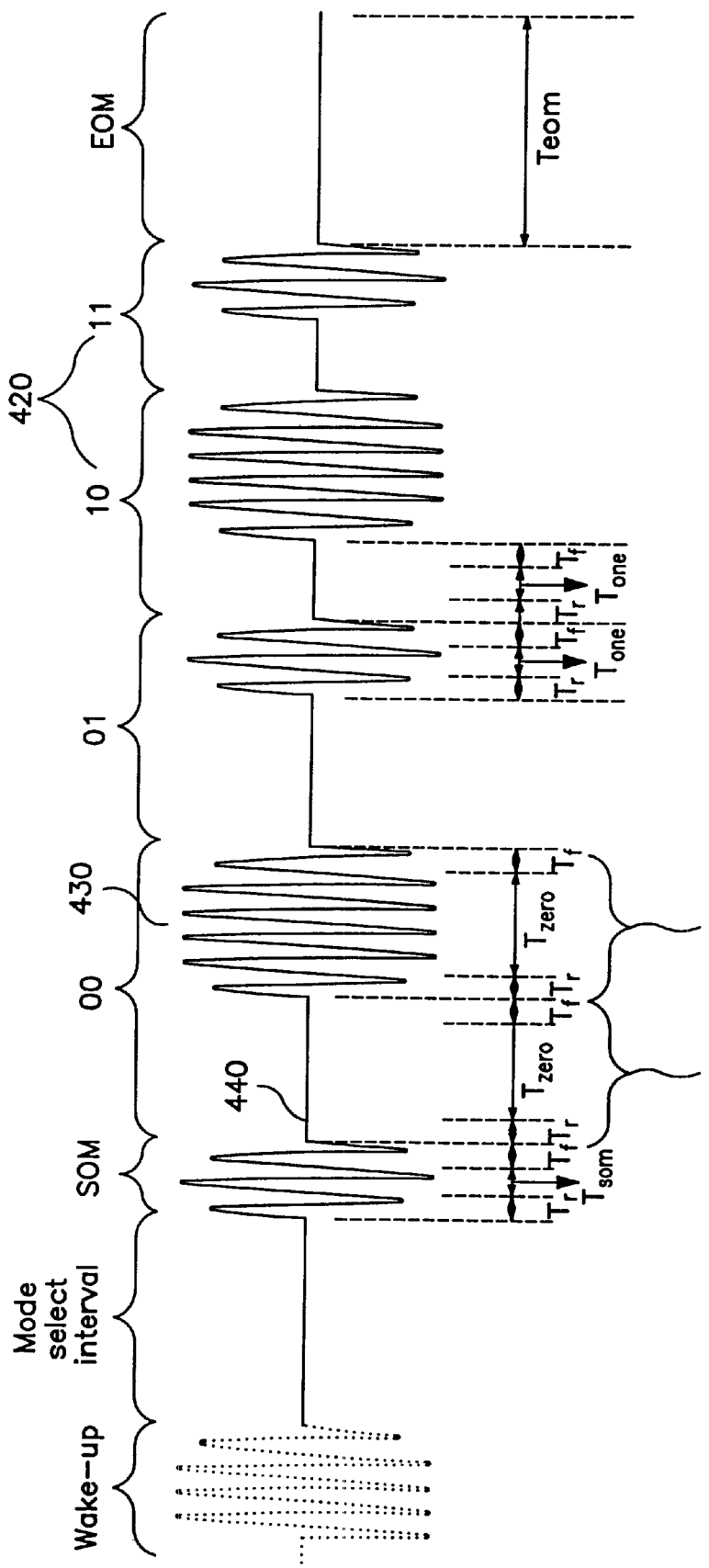
FIG. 9 shows in greater detail a preferred configuration for the data portion of the message envelope for Format B communication in the telemetry system of the present invention.

FIG. 9 shows in greater detail a preferred format for the data 370 portion of a message envelope 330 (shown in FIG. 7) for modulation Format B communication in the telemetry system. Format B uses pulse or burst width modulation (PWM) plus pulse interval modulation (PIM) and is preferably used in combination with medical devices having a data rate capability of Class II. The data transmissions using Format B are also based on variable width bursts of 175 kHz transmitted at a constant rate. In addition, Format-B modulates the interval between bursts to effectively double the amount of data transmitted per unit of time. Format B is a "performance" format. The Format B/Class II combination in the telemetry system is a higher speed communications configuration. This configuration is labeled "Configuration-2" in FIG. 5.

As shown in FIG. 9, data bits are transmitted in pairs or "dibits" 420 in Format B. Each bit is represented by a burst 430 or a "not burst" 440. The bit timing for either type of bit is the same. As an example, a time interval of $T_{zero}$ can represents a zero bit for either of the states, burst 430 or not burst 440.

In a preferred embodiment of Format B, the first bit 450 of each dibit begins with a "not burst" 440. The size of the not burst is simply the length of time measured from the end of the previous burst to the start of the next ($T_{zero}$ or $T_{one}$). The second bit 460 of the dibit is a burst. This period is measured from the start to the end of a burst. Those skilled in the art will readily recognize that the "not burst"-burst sequence of the first and second bits can be easily varied, for example into burst-"not-burst" sequence.

Another preferred modulation format for the data 370 portion of a message envelope 330 (shown in FIG. 7) that will allow telemetry communication is modulation Format C. Format C involves modified BPSK protocol and is preferably used in combination with medical devices having a data rate capability of Class III. The Class III/Format-C configuration in the telemetry system is a "high performance" configuration and is labeled as "Configuration-3" in FIG. 6.

Other modulation modulation formats that can be used in the telemetry system of the present invention include a pulse position modulation (PPM) format and a pulse interval modulation (PIM) with a corresponding data rate capability.

Certain preferred embodiments of the telemetry system of the present invention have been described with reference to FIGS. 5–8 referring to telemetry communication between a programmer and a medical device. However, those skilled in the art will readily recognize that there the telemetry system can also be used to facilitate telemetry communication between programmers or only between medical devices.

In addition, embodiments of the telemetry system of the present invention were described with reference to telemetry communication between a programmer and a medical device. Those of skill in the art will recognize that the telemetry system can be used with any number of medical devices that are external or implantable. As such, the telemetry system can be used with any number of medical devices including, but not limited to, an Implantable Neuro Stimulators (INS), an External Neuro Stimulators (ENS), a pacemakers, a defibrillators, a cochlear implants, implantable diagnostic devices for detecting bodily conditions. of certain organs, like the brain or the heart, and drug delivery systems having an implantable drug delivery pump.

It will also be apparent to those of skill in the art that the arrangement and configuration of components used to implement the embodiments described for the telemetry system are merely preferred components. It will be readily apparent that different telemetry components may be used with the telemetry system. For example, the telemetry modules discussed may have use a transceiver instead of the separate receivers and transmitters described. Also, certain components may not be necessary in this system when uni-directional communication is desired.

Those skilled in that art will recognize that the preferred embodiments may be altered or amended without departing from the true spirit and scope of the invention. Thus, while various alteration and permutations are possible, the invention is limited only by the following claims and equivalents.

I claim:

1. A medical device telemetry system comprising in combination:

a medical device having a first telemetry module; and a programmer having a second telemetry module able to transmit a message envelope to the first telemetry module, the message envelope providing indication of at least one modulation protocol configuration that can be used for telemetry communication with the programmer;

wherein the first telemetry module is capable of automatically selecting at least one compatible modulation protocol configuration for telemetry communication between the first and second telemetry modules based upon the message envelope.

2. A medical device telemetry system comprising in combination:

a medical device having a first telemetry module; and a programmer having a second telemetry module able to transmit a message envelope to the first telemetry module;

wherein the first telemetry module is capable of automatically selecting at least one compatible modulation protocol configuration for telemetry communication between the first and second telemetry modules based upon the message envelope, and wherein the first telemetry module can contemporaneously select a second modulation protocol configuration based upon the message envelope while communicating with the second telemetry module on a first modulation protocol such that the medical device is capable of switching between multiple modulation protocol configurations.

3. The medical device telemetry system of claim 2 wherein the message envelope comprises a configuration select interval and a start-of-message burst.

4. The medical device telemetry system of claim 3 wherein the compatible modulation protocol configuration is symmetric and comprises a modulation format and a data rate capability.

5. The medical device telemetry system of claim 4 wherein the modulation format is pulse width modulation, pulse width modulation plus pulse interval modulation, modified phase shift keying modulation, pulse position modulation or pulse interval modulation.

6. The medical device telemetry system of claim 5 wherein the data rate capability is low speed, medium speed or high speed.

7. The medical device telemetry system of claim 4 wherein the medical device is selected from the group consisting of an internal neuro stimulator, an external neuro stimulator, a pacemaker, a defibrillator, a cochlear implant, an implantable diagnostic device, and an implantable drug delivery pump.

8. A medical device telemetry system comprising in combination:
   a medical device having a first telemetry module; and
   a programmer having a second telemetry module able to transmit a message envelope to the first telemetry module, the message envelope providing indication of at least one modulation protocol configuration that can be used for telemetry communication with the programmer;
   wherein the first telemetry module is capable of automatically selecting at least one compatible modulation protocol configuration for unidirectional communication from the second telemetry module to the first telemetry module based upon the message envelope.

9. A medical device telemetry system comprising in combination:
   a medical device having a first telemetry module; and
   a programmer having a second telemetry module able to transmit a message envelope to the first telemetry module;
   wherein the first telemetry module is capable of automatically selecting at least one compatible modulation protocol configuration for unidirectional communication from the second telemetry module to the first telemetry module based upon the message envelope, and wherein the modulation protocol configuration can contemporaneously select a second modulation protocol configuration based upon the message envelope while in communication with the second telemetry module on a first compatible modulation protocol such that the medical device is capable of switching between multiple protocal configurations.

10. The medical device telemetry system of claim 9 wherein the message envelope comprises a configuration select interval and a start-of-message burst.

11. The medical device telemetry system of claim 10 wherein the modulation protocol configuration is symmetric and comprises a modulation format and a data rate capability.

12. The medical device telemetry system of claim 11 wherein the modulation format is pulse width modulation, pulse width modulation plus pulse interval modulation, modified phase shift keying modulation, pulse position modulation or pulse interval modulation.

13. The medical device telemetry system of claim 12 wherein the data rate capability is low speed, medium speed or high speed.

14. The medical device telemetry system of claim 13 wherein the medical device is selected from the group consisting of an internal neuro stimulator, an external neuro stimulator, a pacemaker, a defibrillator, a cochlear implant, an implantable diagnostic device, and an implantable drug delivery pump.

15. A method for establishing a communications link for transmission of information between a medical device and a programmer, the method comprising:
   transmitting a message envelope to the medical device;
   receiving a message envelope at a telemetry module in the medical device;
   interpreting the message envelope to automatically select a protocol modulation configuration based upon the message envelope; and
   establishing the communications link with a programmer telemetry module using the selected protocol configuration.

16. The method for establishing a communications link of claim 15 wherein the telemetry module can contemporaneously select a modulation protocol configuration based upon the message envelope while communicating with the programmer telemetry module such that the medical device is capable of switching between multiple protocol configurations.

17. The method for establishing a communications link of claim 16 wherein the message envelope comprises a configuration select interval and a start-of-message burst.

18. The method for establishing a communications link of claim 17 wherein the modulation protocol configuration is symmetric and comprised of a modulation format and a data rate capability.

19. The method for establishing a communications link of claim 18 wherein the modulation format is pulse width modulation, pulse width modulation plus pulse interval modulation, modified phase shift keying modulation, pulse position modulation or pulse interval modulation.

20. The method for establishing a communications link of claim 19 wherein the data rate capability is low speed, medium speed or high speed.

21. The method for establishing a communications link of claim 20 wherein the medical device is selected from the group consisting of an internal neuro stimulator, an external neuro stimulator, a pacemaker, a defibrillator, a cochlear implant, an implantable diagnostic device, and an implantable drug delivery pump.

22. A communication modulation protocol configuration for establishing a communications link in a telemetry system between a first telemetry module in a medical device and a second telemetry module in a programmer, the modulation protocol configuration comprising in combination:
   at least one modulation format; and
   a data rate capability for the medical device;
   wherein a first modulation format is automatically selected based upon a message envelope communicated between the first telemetry module and the second telemetry module, wherein the message envelope provides indication of at least one modulation protocol format that can be used for telemetry communication with the programmer.

23. A communication modulation protocol configuration for establishing a communications link in a telemetry system between a first telemetry module in a medical device and a second telemetry module in a programmer, the modulation protocol configuration comprising in combination:
   at least one modulation format; and
   a data rate capability for the medical device,
   wherein a first modulation format is automatically selected based upon a message envelope communicated between the first telemetry module and the second telemetry module, and wherein the automatically selected modulation protocol configuration is symmetric.

24. The communication modulation protocol configuration of claim 23 wherein the first telemetry module can contemporaneously select a second modulation format based upon the message envelope while communicating with the second telemetry module on the first modulation format such that the medical device is capable of switching between multiple modulation formats.

25. The medical device telemetry system of claim 24 wherein the modulation format is pulse width modulation, pulse width modulation plus pulse interval modulation, modified phase shift keying modulation, pulse position modulation or pulse interval modulation.

26. The medical device telemetry system of claim 25 wherein the data rate capability is low speed, medium speed or high speed.

27. The symmetrical modulation protocol configuration of claim 26 wherein the medical device is selected from the group consisting of an internal neuro stimulator, an external neuro stimulator, a pacemaker, a defibrillator, a cochlear implant, an implantable diagnostic device, and an implantable pump.

28. A method for establishing a communications telemetry link between a programmer and a medical device with at least one system layer, the method comprising:
    transmitting a message envelope to the medical device, wherein the message envelope is comprised of a header, a message and a trailer;
    receiving the message envelope at a physical layer in the medical device;
    transmitting the message envelope to a data link layer;
    removing the header and trailer from the message envelope at the data link layer;
    transmitting the message to a network layer;
    transmitting the message to the network layer to an applications layer; and
    interpreting the header in the data link layer to automatically select a protocol modulation configuration for the telemetry link to thereby establish the communications link between the medical device and the programmer using the selected protocol modulation configuration.

29. The method for establishing a communications telemetry link of claim 28 wherein the message envelope comprises a configuration select interval and a start-of-message burst for automatically selecting the symmetrical protocol configuration.

30. The method for establishing a communications telemetry link of claim 29 wherein the modulation protocol configuration is comprised of a modulation format and a data rate capability.

31. The method for establishing a communications telemetry link of claim 30 wherein the modulation format is pulse width modulation, pulse width modulation plus pulse interval modulation, modified phase shift keying modulation, pulse position modulation or pulse interval modulation.

32. The method for establishing a communications telemetry link of claim 31 wherein the data rate capability is low speed, medium speed or high speed.

33. The method for establishing a communications telemetry link of claim 28 wherein the medical device is selected from the group consisting of an internal neuro stimulator, an external neuro stimulator, a pacemaker, a defibrillator, a cochlear implant, an implantable diagnostic device, and an implantable drug delivery pump.

34. A system for establishing a telemetric communications link for transmission of information comprising in combination:
    a programming device capable of transmitting a message envelope via a programmer telemetry module;
    a medical device capable of receiving the message envelope via a medical device telemetry module; and
    means for interpreting the message envelope to automatically select a protocol modulation configuration based upon the message envelope,
    wherein medical device telemetry module is configured to operate in the selected protocol modulation configuration.

35. The system of claim 34, wherein the means for interpreting is selected from the group consisting of a controller and a processor.

36. The system of claim 34, wherein the medical device telemetry module can contemporaneously select a modulation protocol configuration based upon the message envelope while communicating with the programmer telemetry module such that the medical device is capable of switching between multiple protocol configurations.

37. The system of claim 34, wherein the message envelope comprises a configuration select interval and a start-of-message burst.

38. The system of claim 34, wherein the modulation protocol configuration is symmetric and comprised of a modulation format and a data rate capability.

39. The system of claim 38, wherein the modulation format is pulse width modulation, pulse width modulation plus pulse interval modulation, modified phase shift keying modulation, pulse position modulation or pulse interval modulation.

40. The system of claim 38, wherein wherein the data rate capability is low speed, medium speed or high speed.

* * * * *